United States Patent [19]

Nevo et al.

[11] Patent Number: 5,355,889
[45] Date of Patent: Oct. 18, 1994

[54] MONITORING SYSTEM FOR PRODUCING PATIENT STATUS INDICATOR

[75] Inventors: Igal Nevo, Bala Cynwyd; Allon Guez, Penn-Valley, both of Pa.

[73] Assignee: Albert Eisenstein Health Care Foundation, Philadelphia, Pa.

[21] Appl. No.: 895,669

[22] Filed: Jun. 9, 1992

[51] Int. Cl.$^5$ .......................................... A61B 5/0205
[52] U.S. Cl. ..................... 128/671; 128/670
[58] Field of Search ...................... 128/668, 670–672, 128/664–667, 687, 706, 736, 731–732, 716, 721; 364/413.02, 415

[56] References Cited

U.S. PATENT DOCUMENTS

| | | | |
|---|---|---|---|
| 4,796,639 | 1/1989 | Snow et al. | 128/671 X |
| 4,834,107 | 5/1989 | Warner | 128/668 |

OTHER PUBLICATIONS

"A New Patient's Status Indicator To Facilitate Decision Making In Anesthesia," I. Nevo et al., *IEEE Computer-Medical Systems, Proceedings of Fourth Annual IEEE.*
"PONI: An Intelligent Alarm System for Respiratory and Circulatory Management in the Operating Rooms," Paul V. Matsiras, Jun. 1989.
"Integration Concepts for Anesthesia Workstation Displays," Jan J. van der Aa et al., *J. Clin. Monitoring*, 8(2) 1992.
"Anesthesioligit's Adaptive Associate," F. Ahmed et al., *IEEE-EMBS*, Philadelphia, 1990.
"Vital Function Status-A Comprehensive Display To Enhance Decision Making in Anesthesia and ICU," Nevo et al., *Rotterdam*, Oct. 1990.
"Vital Function Status-A Parameter to Facilitate Decision Making in Anesthesia," I. Nevo et al., *Orlando* Jan. 1991.
"A Knowledge-Based Approach to Intelligent Alarms in Anesthesia," Th. Schecke et al., *IEEE-EMBS*, Dec., 1991, pp. 38–44.

*Primary Examiner*—Angela D. Sykes
*Attorney, Agent, or Firm*—Woodcock Washburn Kurtz Mackiewicz & Norris

[57] ABSTRACT

Patient monitoring methods comprising the steps of measuring a plurality of medical parameters, transforming each medical parameter to a function indicative of at least normal and critical levels of the parameter, comparing each function to a prescribed sequence of reference values and on the basis of the comparison generating for each parameter a corresponding danger level, selecting one of the danger levels as a vital function status (VFS) indicator, and displaying the VFS indicator. Each parameter is transformed to a sigmoid function in accordance with pre-selected maximum and minimum values and a pre-selected baseline value adapted to the patient being monitored. A maximum value of the danger levels is selected as the VFS indicator. The VFS indicator will be such that any physician can have, without any previous knowledge of the patient, a reasonably good idea as to the condition of the patient.

17 Claims, 2 Drawing Sheets

MONITORING SYSTEM FOR PRODUCING PATIENT STATUS INDICATOR

FIELD OF THE INVENTION

The present invention generally relates to the field of medical monitoring and more particularly relates to methods and apparatus for monitoring a patient undergoing surgery or intensive care and providing in real time a single parameter reflecting the overall condition of the patient. The present invention may be advantageously employed in a system such as one of the type disclosed in "A New Patient's Status Indicator To Facilitate Decision Making In Anesthesia," I. Nevo et al, *IEEE Computer-Medical Systems, Proceedings of Fourth Annual IEEE Symposium*, pp. 88–93, May 12–14, 1991, which is incorporated by reference into this specification.

BACKGROUND OF THE INVENTION

Medical monitoring systems have greatly improved over the past thirty years. There is, however, much room for improvement, particularly in the manner in which the medical data is presented to the physician. For example, it has been estimated that in the United States between 2,000 and 10,000 patients die every year from causes related to anesthesia, a field in which the present invention is especially useful. Anesthesia-related accidents are typically caused by human error, equipment failure, surgical events, or unexpected alterations in the patient's homeostasis. It is believed that many accidents could be avoided by transforming, in real time, the plethora of information provided to the physician into a more manageable tool for assisting the physician in making a diagnosis of the patient's current condition.

Although equipment failure still causes some accidents, the greatest number of anesthesia-related accidents can be attributed to human error. The process of selecting the correct treatment is performed by the physician under stress, under high mental load and in conditions of uncertainty. Inexperience and fatigue can further undermine the physician's performance. Moreover, the variable and idiosyncratic nature of the patient's physiology contributes substantially to the complexity of the environment. It has been concluded that monitors need to be observed at least every thirty seconds in order for critical events to be detected at an early stage. The physician must divide his or her attention among treating the patient, observing the scattered and intermittent data and monitoring the surgical field. This can cause a delay in the detection and treatment of dangerous conditions.

More than thirty different physiological parameters (e.g., heart rate, blood pressure, cardiac output) are typically measured in the operating room or intensive care unit (ICU) by a number of medical monitors. The medical monitors currently in use are prone to generate false alarms, reducing the physician's responsiveness. A further problem with such monitors is that the data is presented in a confusing manner, i.e., many disparate parameters are displayed in various locations around the physician. Newer monitoring systems integrate the functions of several monitors in one unit, however these provide a congested, confused display. In addition, these monitors have a limited signal processing capability, so their display, which is of short duration, is presented after a time delay.

The dynamic nature of the operating room or ICU environment underscores the need for a system for rapidly presenting useful and comprehensible information to the physician, and quick reaction by the physician, to prevent undesired consequences to the patient. In addition, the physician should be able to identify the primary effector whenever there is a change in the patient's status. This is because knowledge of the primary effector, or the first physiological parameter that varies from its baseline (homeostatic) state, may reveal the patient's true problem. An inability to rapidly detect which physiological parameter first varies from its baseline state may prevent the optimal, causal directed, treatment from being provided.

The aforementioned paper outlines a system that overcomes some of the above-described shortcomings of known medical monitoring systems. Referring to FIG. 1, this system comprises a variety of sensors 10 adapted to be attached to a patient being monitored, a plurality of medical monitors 12 for measuring a plurality of medical parameters indicative of the condition of the patient, a data acquisition module 14, a feature extracting module 16, a vital function unit (VFU) 18, a reference value unit 20, an adaptive inference unit (AIU) 22, and a display 24. The medical monitors 12 are interfaced with the vital function unit 18 by the data acquisition module 14 and feature extraction module 16. The data acquisition module 14 runs as a separate background module that collects and transfers the data to the feature extraction module 16. The feature extraction module 16 extracts relevant features (maximum value, minimum value, etc.) from all input values (heart rate, blood pressure, etc.). All of the collected data is transferred to the AIU 22 and VFU 18. One embodiment of this system has been developed on a 386/33 Mhz platform equipped with an 80387 mathematical co-processor.

The vital function unit 18 is the subsystem that has been developed to facilitate the early identification of the patient's physiological changes. The operation of the VFU 18 is based on the fundamental concept of homeostasis. Under this concept, the patient is regarded as an aggregate of interdependent subsystems (cardiovascular, respiratory, etc.) that interact with each other. It is recognized that a malfunction of one subsystem may cause another subsystem to malfunction as well, and that yet another subsystem may react so as to complicate or mask these malfunctions. The physician is presented a set of physiological parameters (data) that have departed from their baseline values.

The physician usually first attempts to evaluate the severity of the patient's status and to determine whether the patient's condition has improved or deteriorated and to what extent and at what speed any changes have occurred. The assessment of severity should not be confused with the diagnosis, which is the next step and requires more time. All of the parameters are equally important in detecting changes in the patient's condition. In assessing the severity of the patient's status, the direction of deviation of a specific parameter is relatively unimportant; however, the extent and rate of change are important. The direction of deviation is more meaningful in making the correct diagnosis, while the extent and rate of, change are less important.

The primary task of the VFU 18 is to produce a new indicator, the vital function status (VFS) indicator.

Another task of the VFU is to identify the first parameter that deviated from its baseline state. The measured and the calculated values of all the physiological parameters are compared to reference values stored in the reference value unit 20. The values in the reference value unit 20 may be pre-implemented in the system, with different values being assigned in accordance with the patient's age and/or specific problems (for example, hypertension). The physician is able to select specific reference values for each parameter. In other words, the system will utilize for blood pressure the appropriate reference values for hypertension if the patient is a young hypertensive adult, yet reference values for other parameters will be based upon the patient's age group, without consideration of the hypertension.

Each parameter is assigned one of six levels of danger, ranging from zero to 5 according to the following scale:

0=no danger
1=caution
2=alert
3=serious
4=severe
5=critical danger.

FIG. 2 is an example of a display provided by the system. All of the calculated functions are merged to produce the VFS, a numeric indicator whose value similarly ranges from zero to 5, using the scale described above. The graphically displayed VFS indicator provides a semi-quantitative overall assessment of the patient's status. The display comprises a first graph 30 that depicts the history of the VFS over a two minute time span and is periodically updated, for example every second. A second graph 32 depicts the history of the VFS over the last thirty minutes and is also updated every second. Each plot is divided into six equal horizontal arrays, each array having a different color. A text message 34 appears in a third window; this message identifies the first parameter that deviated from its baseline.

The above-described system and its associated display provide a framework for a system with which the physician could detect the nature of a problem in evolution. Moreover, undesired conditions could be anticipated and quickly treated. However, one shortcoming of the system is that it lacks an efficient and effective method for transforming the measured data into the single VFS indicator. The present invention provides this missing element.

SUMMARY OF THE INVENTION

The present invention encompasses patient monitoring methods comprising the steps of measuring a plurality of medical parameters, transforming each medical parameter to a function indicative of at least normal and critical levels of the parameter, comparing each function to a prescribed sequence of reference values and on the basis of the comparison generating for each parameter a corresponding danger level, selecting one of said danger levels as a VFS indicator, and displaying the VFS indicator.

In preferred embodiments of the invention, each parameter is transformed to a sigmoid function in accordance with pre-selected maximum and minimum values and a pre-selected baseline value adapted to the patient being monitored. The basic equation for the sigmoid function employed in this embodiment is as follows:

$$f(x) = \frac{1}{1 + e^{-G(x-BL)}}$$

where BL is the baseline value of the medical parameter x for which the function f(x) is equal to 0.5. The parameter G is determined on the basis of the desired value of f(x) for some other value of x. As described below, other functions, including other sigmoid functions, may be employed as well. In one embodiment of the invention a maximum value of the danger levels is selected as the VFS indicator. In addition, preferred embodiments of the invention may further comprise the step of simultaneously displaying a history of the VFS indicator over a predefined short time span and over a predefined long time span.

The present invention also encompasses patient monitoring systems comprising a plurality of medical monitors operative to measure a plurality of medical parameters, means for transforming each medical parameter to a function indicative of at least normal and critical levels of the parameter, means for comparing each of the functions to a prescribed sequence of reference values and on the basis of the comparison generating for each parameter a corresponding danger level, means for selecting one of said danger levels as a VFS indicator, and means for displaying the VFS indicator.

Another embodiment of the present invention comprises: a plurality of medical monitors, each monitor including means for measuring a medical parameter indicative of a condition of a patient being monitored; a computer operatively coupled to the medical monitors, the computer being programmed to determine for each medical parameter, in accordance with a corresponding baseline value for each parameter, a corresponding danger level ranging from a pre-selected minimum value to a pre-selected maximum value and to select one of said danger levels as a VFS indicator; and means for simultaneously displaying a history of the VFS indicator over a preselected short time span and over a preselected long time span. The computer may advantageously be programmed to transform each medical parameter to a sigmoid function and to assign a danger level to each parameter by comparing the respective values of the sigmoid functions to a prescribed set of reference values and assigning said danger levels on the basis of the comparison.

In preferred embodiments of the invention the transformed values are assigned danger levels by comparing the transformed values to prescribed reference values and assigning the danger level corresponding to the reference values that the transformed value falls between. Thus, in preferred embodiments of the invention each measured parameter is transformed to a value (i.e., a function); the value of the function is compared to known reference values and, depending upon what two reference values the function falls between, a danger level is assigned to the parameter. Exemplary reference values are shown in the following table.

| Reference Values | Danger Level |
| --- | --- |
| 0.42–0.5, 0.5–0.58 | 0 |
| 0.34–0.42, 0.58–0.66 | 1 |
| 0.26–0.34, 0.66–0.74 | 2 |
| 0.18–0.26, 0.74–0.82 | 3 |
| 0.1–0.18, 0.82–0.9 | 4 |

-continued

| Reference Values | Danger Level |
| --- | --- |
| 0–.1, .9–1.0 | 5 |

An advantageous feature of the sigmoid transform employed by preferred embodiments of the invention is that the transformed parameters can be directly compared with one another in determining the VFS indicator. Other important features of the sigmoid transform are that it has a maximum sensitivity (gain or slope) for parameter values near baseline and that it can be defined with variables that can be memorized by the system and employed to transform the measured data in real time using relatively simple formulas. In addition, the sigmoid transform may be applied in a different manner for parameter values below and above the baseline value, which is advantageous in transforming physiological parameters that may have baseline values skewed closer to the minimum value than to the maximum value, or vice versa. Other features of the invention are described below.

DETAILED DESCRIPTION OF PREFERRED EMBODIMENTS

According to the present invention, the individual measured parameters are transformed to normalized data (normalized functions) that can be used by the system to generate the VFS indicator. Each function has a maximum sensitivity where its corresponding parameter begins to become abnormal, as opposed to after it has already become abnormal. In addition, the transformation is relatively simple to carry out. Thus, the VFS indicator can be calculated on-line, in real time. Further, the transformation can be made to be dependent upon both the particular patient and the particular physician. The physician will thus have an intuitive as well as empirical understanding of how his or her decisions regarding the patient will influence how the transformation is performed.

Figure 1:
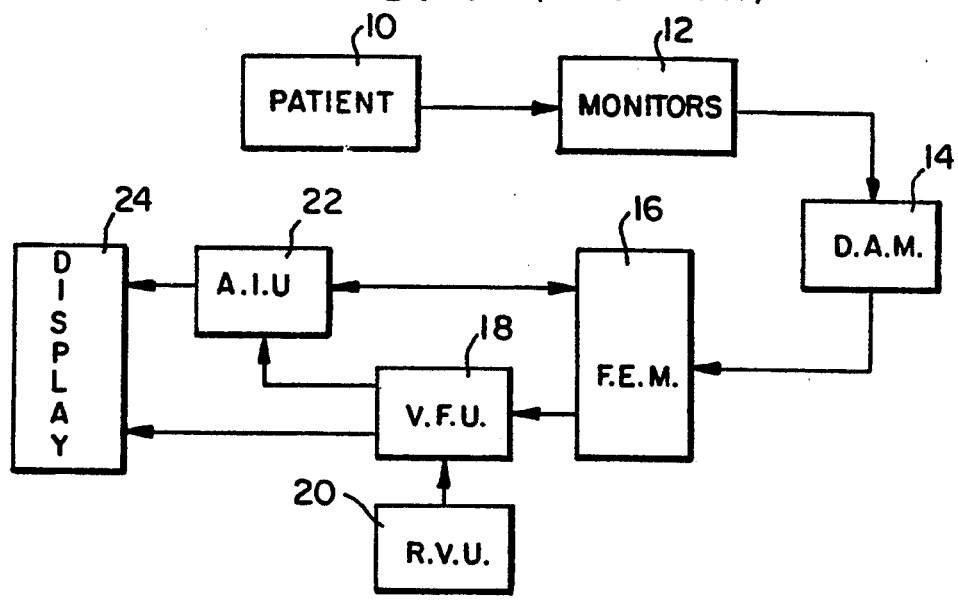
FIG. 1 is a block diagram of a prior art patient monitoring system.
Figure 2:
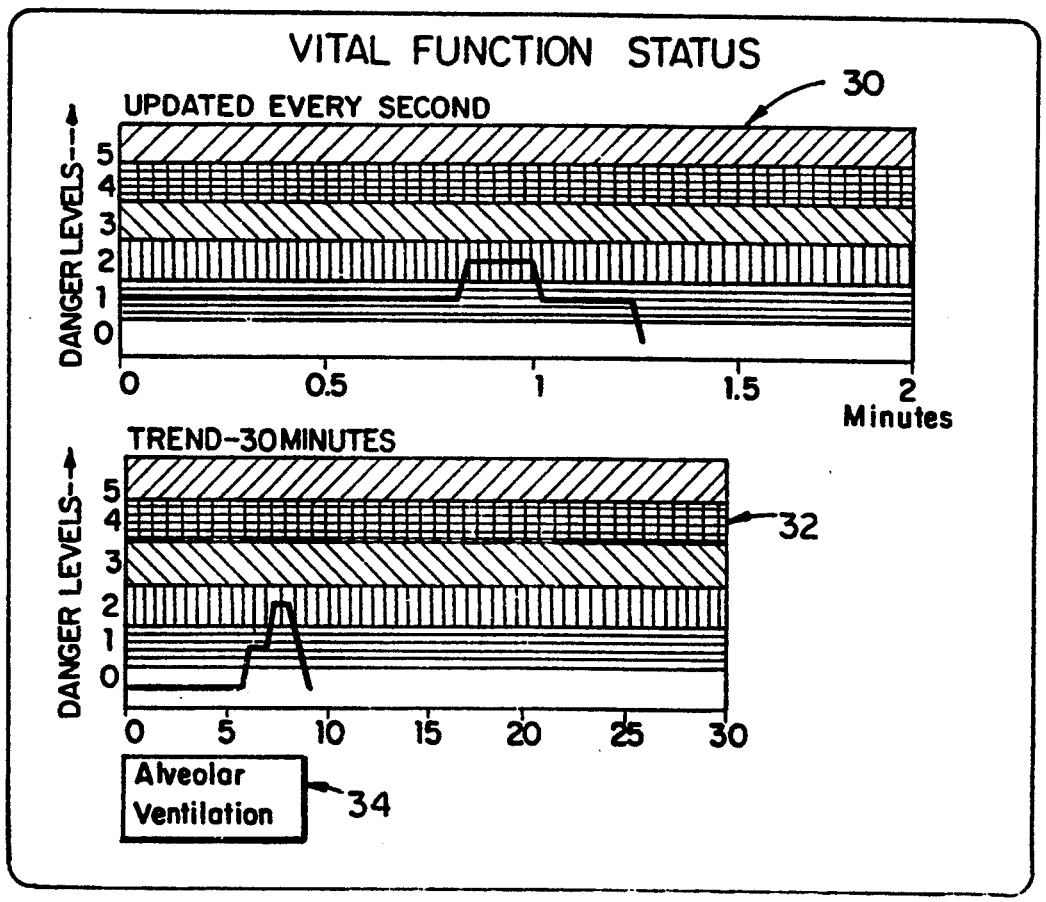
FIG. 2 is an exemplary display provided by the system of FIG. 1.
Figure 3:
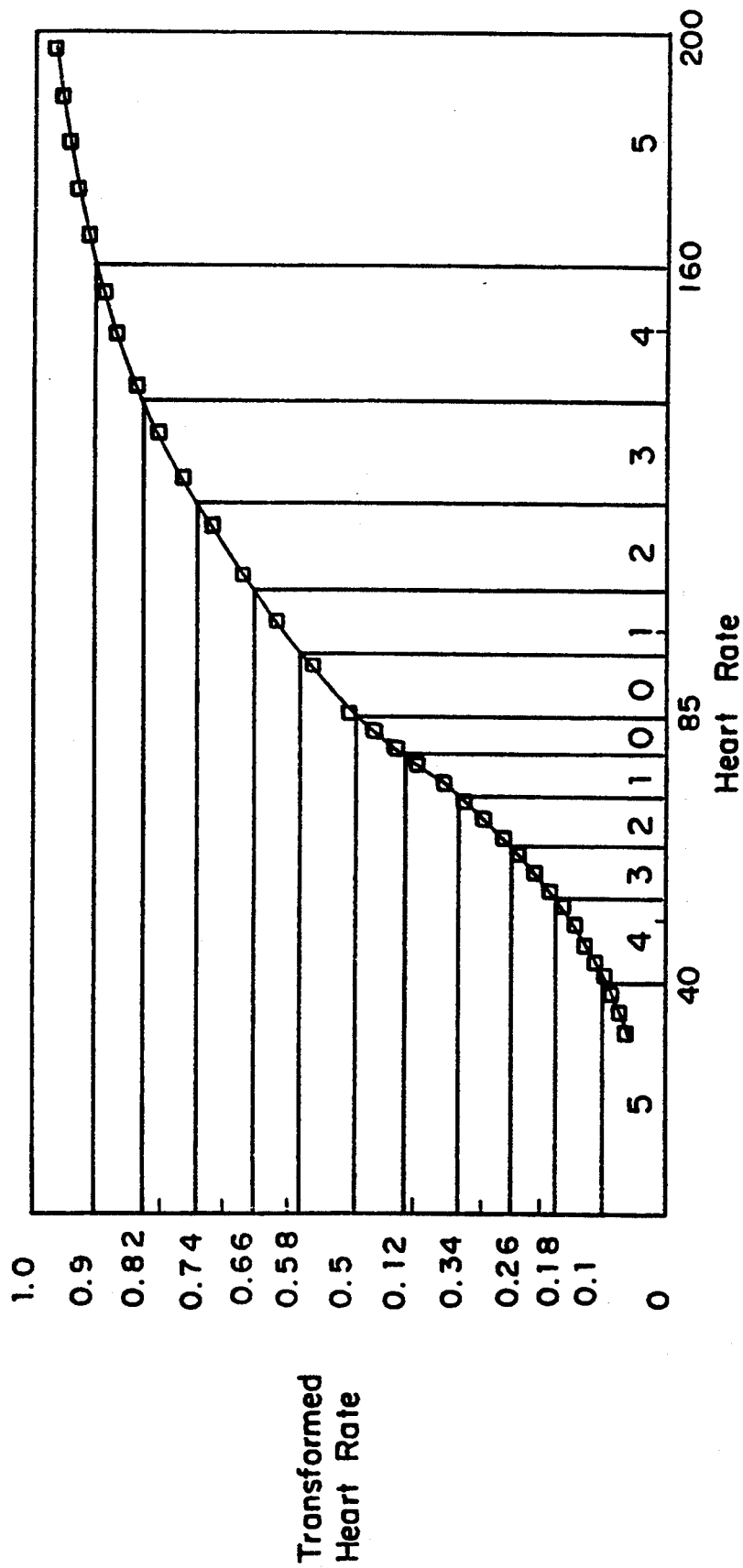
FIG. 3 is an exemplary graph showing one monitored parameter (heart rate) transformed in accordance with the present invention into a function indicative of normal and critical levels of said parameter and levels therebetween.

The transformation is based on the well known sigmoid function. FIG. 3 illustrates how the transformation works. Assume the patient has a normal, or baseline, heart rate of 85 beats per minute (BPM). The physician inputs information regarding what he or she considers to be the baseline values of the various parameters being monitored. (FIG. 3 only illustrates the transformation of heart rate values. However, the transformation is identically performed for all parameters; only the baseline and max/min values are changed.) The physician may be given the option to either create a new patient profile or to recall an old one. Baseline values are mapped to a value of 0.5. When the parameter (e.g., heart rate) goes above the baseline value, it is mapped to a value above 0.5 and below 1.0; values below baseline are mapped to values below 0.5 and above 0.0. In addition, there are maximum and minimum values for each parameter that may advantageously be assumed to be the same for all patients. That is, there are parameter limits that apply to the values of any patient. For heart rate, the minimum and maximum values may be set to 40 and 160 BPM. The transformation maps the minimum value (40) to 0.1 and maps the maximum value (160) to 0.9, as shown in FIG. 3.

Thus, the transformation maps the parameter space of the patient into numbers representing the state of each parameter relative to the patient's homeostatic condition and to prescribed maximum and minimum reference values for each parameter. It is a generally accepted fact that a heart rate of 40 is just above the lower limit for that parameter. A heart rate around 40 BPM indicates a serious medical problem. However, a heart rate of 55 BPM could be considered normal for some patients. This does not leave much room for the heart rate to dip below 55 BPM before the patient is judged to be in a serious medical condition. Referring to FIG. 3, this is exactly what the graph indicates. That is, the function changes significantly as the heart rate dips below 55 BPM. On the other hand, the transformation does allow the patient's heartbeat to vary upward because there is more space between 55 BPM and 160 BPM. The maximum sensitivity is right around the baseline value of 85 BPM.

The basic equation for the sigmoid function employed in this embodiment is as follows:

$$f(x) = \frac{1}{1 + e^{-G(x-BL)}}$$

where BL is the baseline value of the medical parameter x for which the function f(x) is equal to 0.5 (in general, it is preferable to choose the midrange of the sigmoid function as the baseline). The parameter G is determined on the basis of the desired value of f(x) for some other value of x. G is determined with the equation:

$$G = \frac{-\ln\left(\frac{1}{f(x)} - 1\right)}{(x - BL)}$$

According to one embodiment of the present invention, the value of G for all functional values below baseline and the value of G for all functional values above the baseline are derived by setting x equal to its minimum and maximum values, respectively, and mapping these values to 0.1 and 0.9, using the baseline value BL equal to 0.5. (There will only be one value of it G if the baseline value is centered between the maximum and minimum values, i.e., if the function is symmetric about the baseline value.) For any parameter x, the maximum and minimum values are typically known. Therefore, given the baseline value BL of any parameter, the following values are determined:

$$G_{low} = \frac{-\ln\left(\frac{1}{0.1} - 1\right)}{(xmin - BL)}$$

$$G_{high} = \frac{-\ln\left(\frac{1}{0.9} - 1\right)}{(xmax - BL)}$$

$G_{low}$ and $G_{high}$ may be determined before beginning the operating room procedure and thereafter used to determine the value of f(x) in real time during the procedure. Preferred embodiments of the invention transform the measured data in real time in accordance with the following equations:

$$f(x) = \begin{array}{c} \dfrac{1}{1 + e^{-G_{low}(x-BL)}} x \leq BL \\ \dfrac{1}{1 + e^{-G_{high}(x-BL)}} x > BL \end{array}$$

This transformation may be performed upon every parameter measured by the system, since there is a corresponding value of $G_{low}$, $G_{high}$ and BL for every parameter.

The use of the sigmoid function as described above provides several advantages. First, the transformation provides maximum sensitivity (or gain) for parameter values (x) near the parameter's baseline value. The value of f(x) will change most rapidly when the corresponding parameter moves away from the baseline value and will change least rapidly when the parameter is far away from its baseline value. In addition, the data needed to calculate or recalculate the transformed data can be easily and quickly determined. The system may advantageously be programmed such that the baseline profile data may be modified on line. In this case, the system will be adaptable to any patient, taking into account the patient's particular physiology, and to the particular physician involved in the operating room procedure. The maximum and minimum values could also be modified on line.

The VFS indicator is a scaler indicator that signifies the clinical level of danger the patient is in. In preferred embodiments of the invention the VFS indicator is assigned one of six values, ranging from zero to five. Zero represents homeostatic stability and five represents critical danger. On the display, the area representing each danger level increases as the level gets further from the baseline (i.e., the gain or sensitivity of the transformation decreases as the measured parameter moves away from its baseline level). The transformation is performed on every parameter, therefore there is an assigned danger level for each parameter.

In one preferred embodiment of the invention, the value of the VFS indicator is taken to be the maximum danger level of the transformed parameters. As indicated by FIG. 3, the transformed values are assigned danger levels by comparing the transformed values to prescribed reference values and assigning the danger level corresponding to the reference values that the transformed value falls between. Exemplary reference values are shown in the following table.

| Reference Values | Danger Level |
| --- | --- |
| 0.42–0.5, 0.5–0.58 | 0 |
| 0.34–0.42, 0.58–0.66 | 1 |
| 0.26–0.34, 0.66–0.74 | 2 |
| 0.18–0.26, 0.74–0.82 | 3 |
| 0.1–0.18, 0.82–0.9 | 4 |
| 0–.1, .9–1.0 | 5 |

The above reference values may easily be adjusted by the user to meet the specific needs of the patient.

Another feature of one system in accordance with the present invention is that the system analyzes all the measured parameters and identifies the subsystem(s) affected. The result of the analysis is automatically displayed in real time. As an example, suppose a clinical problem affects the respiratory and the cardiovascular subsystems. The monitoring system continues to display the VFS indicator, the causal parameters and the affected subsystems. The procedure is as follows: A VFS vector comprising unit members, each with a discrete value between zero and five, is formed. The individual members of the vector are part of a subvector that represents a subsystem. For example, five unit-members represent the respiratory subsystem; the other four represent the circulation subsystem. A vector of the order 1x6 representing the six major subsystems (actually there are more than six) may be defined. The value of each member (on a scale of , e.g., 0 to 5) of the new vector is the maximum value of the VFS unit-members that relate to the respective subsystem. $VFS_{1,4-7}$ may all be unit-members related to circulation. $VFS_{1-3,8-10}$ may be unit-members related to respiration. Some units (e.g., oxygen concentration or oxygen saturation) may pertain to two or more subsystems. A simple rule can be used to solve this problem. Therefore, the new vector may have one member related to circulation and another related to respiration. If $VFS_{1,3,8,9}$ have a value of "1," and $VFS_{4,5,6}$ have a value of "2," the VFS will be assigned "2." Because of the new vector, the circulation subsystem will be assigned "2" and the respiration subsystem will be assigned "1."

The VFS may be displayed along with an indication of the two subsystems involved. Each of these subsystems, however, will be represented with its sub-VFS, respectively "2" and "1." The advantage of this is that it minimizes the null-space and eliminates ambiguity. The process may be mathematically performed through vector reduction.

The true scope of the present invention is not limited to the transformation of the measured parameters to values ranging from zero to one, nor is the invention limited to the partition of the transform space into six danger levels. Indeed, the invention may be carried out using a transformation other than the sigmoid transform described herein (although the sigmoid is one presently preferred transform). As indicated above, an advantageous feature of the sigmoid transform is that the transformed parameters can be directly compared with one another in determining the VFS indicator. Other important features of the sigmoid transform are that it has a maximum sensitivity (gain or slope) for parameter values near baseline and that it can be defined with only three variables ($G_{low}$, $G_{high}$ and BL), which can be memorized by the system and employed to transform the measured data in real time using relatively simple formulas. In addition, the sigmoid transform may be applied in a different manner (using a different value of G) for parameter values below and above the baseline value, which is advantageous in transforming physiological parameters that may have baseline values skewed closer to the minimum value than to the maximum value, or vice versa. Any transformation with these or similar features may be employed in practicing the present invention.

Instead of the specific sigmoid function specified above, the measured physiological parameters may be normalized by utilizing other functions, such as:

$$y = \tanh(x)$$

-continued $$y = \frac{x}{(1+x)}$$

$$y = \begin{array}{ll} ax + b\sin w|x| > |bw| \\ y_m \quad x > x_{max} \end{array}$$

The function preferably should:
be compact on an infinite domain,
be monotonically increasing or decreasing, and
have a definite derivative (unipolar).

What is claimed is:

1. A patient monitoring method, comprising the steps of:
   (a) measuring a plurality of medical parameters;
   (b) transforming each medical parameter to a sigmoid function indicative of at least normal and critical levels of the parameter;
   (c) comparing each of said functions to a prescribed sequence of reference values and on the basis of the comparison generating for each parameter a corresponding danger level;
   (d) selecting one of said danger levels as a vital function status (VFS) indicator; and
   (e) displaying said VFS indicator.

2. The method of claim 1, wherein each parameter is transformed to a sigmoid function in accordance with pre-selected maximum and minimum values and a pre-selected baseline value adapted to the patient being monitored.

3. The method of claim 2, wherein a maximum value of said danger levels is selected as said VFS indicator.

4. The method of claim 2, comprising the step of simultaneously displaying a history of said VFS indicator over a predefined short time span and over a predefined long time span.

5. The method of claim 1, wherein a maximum value of said danger levels is selected as said VFS indicator.

6. The method of claim 1, comprising the step of simultaneously displaying a history of said VFS indicator over a predefined short time span and over a predefined long time span.

7. A patient monitoring method as recited in claim 1, wherein said transforming employs an equation from the following group:

$$y = \frac{1}{1 + e^{-G(x-BL)}}$$

$$y = \tanh(x)$$

$$y = \frac{x}{(1+x)}$$

$$y = \begin{array}{ll} ax + b\sin w|x| > |bw| \\ y_m \quad x > x_{max} \end{array}$$

wherein x represents the measured value of the medical parameter; BL represents the baseline value for the medical parameter; $x_{max}$ represents a predefined maximum value of the medical parameter; a, b, and w represent predefined numbers; and y represents the value of the function, and $Y_m$ represents a predefined maximum value of the function.

8. A patient monitoring system, comprising:
   (a) a plurality of medical monitors operative to measure a plurality of medical parameters of a patient, each said medical parameter having a predefined baseline or homeostatic value;
   (b) means for transforming each medical parameter to a function indicative of at least normal and critical levels of the parameter;
   (c) means for comparing each of said functions to a prescribed sequence of reference values and on the basis of the comparison generating for each parameter a corresponding danger level;
   (d) means for selecting one of said danger levels as a vital function status (VFS) indicator; and
   (e) means for displaying said VFS indicator;
   wherein said means for transforming employs a member of the following group:
   a sigmoid function.

$$y = \frac{1}{1 + e^{-G(x-BL)}}$$

$$y = \tanh(x)$$

$$y = \frac{x}{(1+x)}$$

$$y = \begin{array}{ll} ax + b\sin w|x| > |bw| \\ y_m \quad x > x_{max} \end{array}$$

wherein x represents the measured value of the medical parameter; BL represents the baseline value for the medical parameter; $x_{max}$ represents a predefined maximum value of the medical parameter; a, b, and w represent predefined numbers; and y represents the value of the function, and $y_m$ represents a predefined maximum value of the function.

9. The system of claim 8, comprising means for transforming each parameter to a sigmoid function in accordance with pre-selected maximum and minimum values and a pre-selected baseline value adapted to the patient being monitored.

10. The system of claim 9, comprising means for selecting a maximum value of said danger levels as said VFS indicator.

11. The system of claim 9, comprising means for simultaneously displaying a history of said VFS indicator over a predefined short time span and over a predefined long time span.

12. The system of claim 8, comprising means for selecting a maximum value of said danger levels as said VFS indicator.

13. The system of claim 8, comprising means for simultaneously displaying a history of said VFS indicator over a predefined short time span and over a predefined long time span.

14. A medical monitoring system, comprising:
   (a) a plurality of medical monitors, each monitor including means for measuring a medical parameter indicative of a condition of a patient being monitored, each medical parameter having a baseline value;
   (b) a computer operatively coupled to said medical monitors, said computer being programmed to determine for each medical parameter a corresponding danger level and to select one of said danger levels as a vital function status (VFS) indicator; wherein, in determining said danger levels, each medical parameter is transformed to a function defined by pre-selected maximum and minimum parameter values and a pre-selected baseline value, said function exhibiting a maximum sensitivity for parameter values near said baseline; and (c) means for simultaneously displaying a history of said VFS indicator over a predefined short time span and over a predefined long time span;

wherein said computer is programmed to transform said medical parameters by employing a member of the following group:

a sigmoid function.

$$y = \frac{1}{1 + e^{-G(x-BL)}}$$

$$y = \tanh(x)$$

$$y = \frac{x}{(1 + x)}$$

$$y = \begin{array}{l} ax + b\sin w|x| \quad > \quad |bw| \\ y_m \quad x > x_{max} \end{array}$$

wherein x represents the measured value of the medical parameter; BL represents the baseline value for the medical parameter; $x_{max}$ represents a predefined maximum value of the medical parameter; a, b, and w represent predefined numbers; and y represents the value of the function, and $y_m$ represents a predefined maximum value of the function.

15. The system of claim 14, wherein said computer is programmed to transform each medical parameter to a sigmoid function and to assign a danger level to each parameter by comparing the respective values of the sigmoid functions to a prescribed set of reference values and assigning said danger levels on the basis of the comparison.

16. The system of claim 15, wherein said danger levels are assigned in accordance with the following table:

| Transformed Values | Danger Level |
| --- | --- |
| 0.42–0.5, 0.5–0.58 | 0 |
| 0.34–0.42, 0.58–0.66 | 1 |
| 0.26–0.34, 0.66–0.74 | 2 |
| 0.18–0.26, 0.74–0.82 | 3 |

-continued

| Transformed Values | Danger Level |
| --- | --- |
| 0.1–0.18, 0.82–0.9 | 4 |
| 0–.1, .9–1.0 | 5 |

17. A patient monitoring method, comprising the steps of:

(a) measuring a plurality of medical parameters of a patient;

(b) transforming each medical parameter to a function indicative of at least normal and critical levels of the parameter, wherein said functions have common maximum and minimum values, wherein each said function is defined by a pre-selected baseline value adapted to said patient, and wherein each said function exhibits a maximum sensitivity or slope for parameter values near said baseline;

(c) comparing each of said functions to a prescribed sequence of reference values and on the basis of the comparison generating for each parameter a corresponding danger level;

(d) selecting one of said danger levels as a vital function status (VFS) indicator; and (e) displaying said VFS indicator;

wherein said transforming employs a member of the following group:

a sigmoid function $$y = \frac{1}{1 + e^{-G(x-BL)}}$$

$$y = \tanh(x)$$

$$y = \frac{x}{(1 + x)}$$

$$y = \begin{array}{l} ax + b\sin w|x| \quad > \quad |bw| \\ y_m \quad x > x_{max} \end{array}$$

wherein x represents the measured value of the medical parameter; BL represents the baseline value for the medical parameter; $x_{max}$ represents a predefined maximum value of the medical parameter; a, b, and w represent predefined numbers; and y represents the value of the function, and $y_m$ represents a predefined maximum value of the function.

* * * * *

UNITED STATES PATENT AND TRADEMARK OFFICE
CERTIFICATE OF CORRECTION

PATENT NO. : 5,355,889
DATED : October 18, 1994
INVENTOR(S) : Igal Nevo and Allon Guez It is certified that error appears in the above-indentified patent and that said Letters Patent is hereby corrected as shown below:

Col. 9, line 64, "$Y_m$" should be --$y_m$--

Signed and Sealed this

Thirty-first Day of January, 1995

*Attest:*

BRUCE LEHMAN

*Attesting Officer*   *Commissioner of Patents and Trademarks*